United States Patent [19]

Cherukuri et al.

[11] 4,317,838

[45] Mar. 2, 1982

[54] METHOD FOR APPLYING SUGARLESS COATING TO CHEWING GUM AND CONFECTIONS

[75] Inventors: Subraman R. Cherukuri; Dominick R. Friello, both of Danbury, Conn.

[73] Assignee: Life Savers, Inc., New York, N.Y.

[21] Appl. No.: 237,336

[22] Filed: Feb. 23, 1981

Related U.S. Application Data

[63] Continuation of Ser. No. 77,968, Sep. 24, 1979, abandoned.

[51] Int. Cl.³ .............................................. A23G 3/30
[52] U.S. Cl. ...................................... 426/5; 426/291; 426/292; 426/303; 426/305
[58] Field of Search ....................................... 426/3-6, 426/103, 291, 292, 295, 303, 305, 804, 548, 658

[56] References Cited

U.S. PATENT DOCUMENTS

| | | | |
|---|---|---|---|
| 2,304,246 | 12/1942 | Ekert | 426/5 |
| 2,305,960 | 12/1942 | Frorer | 426/5 |
| 3,554,767 | 1/1971 | Daum et al. | 426/6 |
| 4,127,677 | 11/1978 | Fronczkowski | 426/5 |

*Primary Examiner*—Jeanette M. Hunter
*Attorney, Agent, or Firm*—Lawrence S. Levinson; Burton Rodney

[57] ABSTRACT

An improved method for applying a sugarless coating containing sorbitol to chewing gum pieces and confections by using a single coating syrup containing sorbitol and/or other non-sugar sweetener, an adhesion or binder component, such as gum arabic, a filler-anti-stick component, such as calcium carbonate, and a dispersing agent, such as titanium dioxide.

13 Claims, No Drawings

METHOD FOR APPLYING SUGARLESS COATING TO CHEWING GUM AND CONFECTIONS

This is a continuation of application Ser. No. 077,968, filed Sept. 24, 1979 now abandoned.

FIELD OF THE INVENTION

The present invention relates to an improved method for applying a sugarless coating containing sorbitol in crystalline form, to a chewing gum, confection, and medicinals and therapeutics in the form of pills or tablets, and to any of the above comestibles containing such a sugarless coating.

BACKGROUND OF THE INVENTION

Candy-coated chewing gums have long been a favorite among young and old alike. The candy coatings generally employed are sugar-based and thus are not used as coatings for sugarless gums. The sugar-based coatings may be applied to chewing gum employing procedures such as described in U.S. Pat. Nos. 3,554,767 to Daum et al, 2,304,246 to Ekert, 2,460,698 to Lindhe and 3,208,405 to Beer.

U.S. Pat. No. 4,127,677 to Fronczkowski et al discloses a xylitol coated chewing gum containing from 95 to 99.5% xylitol which may be used as a coating for sugarless gums. However, for various reasons, xylitol containing chewing gums have not received satisfactory consumer acceptance.

Sorbitol, long used as a plasticizer and sweetener, has been suggested as a substitute for sugar in forming sugarless candy coatings for sugarless chewing gums. Unfortunately, however, it has been found that when sorbitol is applied in an aqueous coating solution to chewing gum centers, the sorbitol does not recrystallize to form a thin crystalline coat. Moreover, the chewing gum centers subjected to the sorbitol chewing step stick to one another forming undesirable clumps.

Accordingly, a need exists in the market place for a sugarless coating, preferably free of xylitol, based on the use of sorbitol.

Copending application Ser. No. 12,999, filed Feb. 21, 1979 discloses a method for forming a sugarless candy coating, preferably including crystalline sorbitol, on chewing gums, confections, and generally in the preparation of candy coated pills, tablets and other solid shapes, which method overcomes the problems associated with the application of sorbitol-containing coatings to produce a uniform sugarless coating, with good appearance, and flavor release and having bite-through and chew properties of a soft crystal. The technique employed for forming a sugarless coating on a solid shape to be coated (hereinafter referred to as centers) includes the steps of applying to the centers a first coating syrup which contains a sweetener such as sorbitol and/or other non-sugar sweetener, for example, mannitol or hydrogenated starch hydrolysate, an adhesion or binder component and a film-forming component, to thereby coat the centers with the first coating syrup, and then applying a dusting mix to the centers coated with the first coating syrup, the dusting mix including one or more sweeteners, such as employed in the first coating syrup, in powdered form, and a moisture absorbing component, such as mannitol, an anti-sticking component such as calcium carbonate and a dispersing agent such as titanium dioxide, and then preferably applying a second coating syrup to smooth out the coating of the centers and provide a shine thereto, which second coating syrup generally includes ingredients similar to that present in the dusting mix but dispersed in water.

The above technique has proved to be an excellent method, albeit, it usually requires two different types of coating syrups to produce the desired coating. Accordingly, a sugarless coating technique wherein only a single coating syrup is employed would be a tremendous advance over the afore-mentioned prior art as well as over the above-described copending application.

DESCRIPTION OF THE INVENTION

In accordance with the present invention, an improved so-called "one step" or "one syrup" method is provided for forming a sugarless coating on a solid shape to be coated (hereinafter referred to as centers) and includes the steps of applying to the centers a coating syrup which contains a sweetener such as sorbitol and/or other non-sugar sweetener, for example, mannitol or hydrogenated starch hydrolysate, an adhesion or binder component and a film-forming component, an anti-sticking (or filler) component, and a dispensing agent, to thereby coat the centers with the coating syrup, and then applying a dusting mix to the centers coated with the coating syrup, the dusting mix including one or more sweeteners, such as employed in the coating syrup, in powdered form, and a moisture absorbing component, an anti-sticking component and a dispersing agent.

The steps of applying the coating syrup and dusting mix will be repeated, as many times as necessary, to build up a desired coating weight and thickness on the centers.

In carrying out the method of the invention, coating syrup will be formed as an aqueous solution of the (a) sweetener (or bulking agent), (b) adhesion or binder component, (c) an anti-sticking (filler) component, and (d) a dispersing agent.

The sweetener (or bulking agent) (a) may be present in an amount within the range of from about 30% to about 70%, preferably from about 40 to about 60% by weight of the coating syrup; the binder (b) may be present in an amount within the range of from about 5 to about 30%, preferably from about 10 to about 25% by weight of the coating syrup; the anti-sticking (filler) agent (c) may be present in an amount within the range of from about 3 to about 15% and preferably from about 5 to about 10% by weight of the coating syrup; and the dispersing agent (d) may be present in an amount of within the range of from about 2 to about 12%, and preferably from about 3 to about 7% by weight of the coating syrup. The coating syrup will also contain from about 20 to about 70%, and preferably from about 25 to about 65% water.

The coating syrup functions as a wet base layer to which later-deposited dry sweetener or bulking agent (present in the dusting mix) may adhere or be absorbed on to form the desired coating.

Examples of sweeteners or bulking agents suitable for use in the coating syrup may comprise substantially any known sugarless sweetener such as any of the sugar alcohols such as sorbitol, xylitol, mannitol, and combinations thereof, with sorbitol being preferred, as well as maltitol, isomaltitol, hydrogenated starch hydrolysates such as those disclosed in U.S. Pat. No. Re. 26,959 as well as various hydrogenated glucose syrups and/or powders which contain sorbitol, hydrogenated disaccharides, tri- to hexa-hydrogenated saccharides, and hydrogenated higher polysaccharides and the modified starch hydrolysates disclosed in U.S. Pat. No. 3,556,811 to Smith.

The hydrogenated glucose syrups and/or powders may be produced by catalytic hydrogenation of standard glucose syrups (acid and/or enzyme converted) to the point where all the glucose end groups of the saccharides are reduced to alcohols, that is, dextrose to sorbitol. In the case of hydrogenated glucose syrups, the total solids contents will range from about 72 to about 80% which solids are made of from about 4 to about 20% sorbitol, from about 20 to about 65% hydrogenated disaccharides (that is, maltitol), from about 15 to about 45% tri- to heptahydrogenated saccharides, and from about 10 to about 35% hydrogenated saccharides higher than hepta.

Other sweeteners or bulking agents suitable for use in the coating syrup include, but are not limited to free saccharin acid, sodium, calcium and ammonium saccharin, cyclamate salts, dihydrochalcones, glycyrrhizin, L-aspartyl-L-phenylalanine methyl ester and mixtures thereof.

The adhesion component or binder employed in the coating syrup aids in initially binding the sweetener to the comestible being coated. Examples of binders suitable for use herein include gum arabic, xanthan gum, gum tragacanth, tapioca dextrin, or modified food starch, with gum arabic being preferred.

The moisture absorbing compound suitable for use herein includes mannitol, or dicalcium phosphate with mannitol being preferred especially when sorbitol is employed as the sweetener.

Examples of the anti-sticking compound which may also function as a filler employed in the coating syrup as well as the dusting mix include calcium carbonate, talc, or magnesium trisilicate, with calcium carbonate being preferred.

Examples of the dispersing agent which may be employed in the coating syrup as well as the dusting agent include titanium dioxide, talc or other anti-stick compounds set out above, with titanium dioxide being preferred.

An optional but important component of the coating syrup is the film-forming agent which enables the deposition of a substantially uniform layer of the sweetener on the comestible being coated. Examples of film-forming agents suitable for use herein include gelatin, methyl cellulose, hydroxypropyl cellulose, ethyl cellulose, hydroxyethyl cellulose, and/or carboxymethyl cellulose.

The dusting mix comprises a dry powder mixture containing (a) sweetener (or bulking agent) similar to (and preferably the same as) that employed in the coating syrup, (b) moisture absorbing component, (c) anti-sticking (or filler) component, and (d) dispersing agent. Components (b), (c) and (d) are employed in a weight ratio to sweetener (a) of within the range of from about 5 to about 30(b):1, from about 2 to about 20(c):1, and from about 0 to about 5(d):1. Thus, the sweetener (a) will be employed in an amount within the range of from about 40 to about 90%, and preferably from about 60 to about 85% by weight of the dusting mix, the moisture absorbing component (b) will be employed in an amount within the range of from about 5 to about 30%, and preferably from about 8 to about 20% by weight of the dusting mix, the anti-sticking component (c) will be employed in an amount within the range of from about 2 to about 20%, and preferably from about 5 to about 15% by weight of the dusting mix, and the dispersing agent will be employed in an amount within the range of from about 2 to about 12%, and preferably from about 4 to about 9% by weight of the dusting mix.

As indicated, the sweetener (bulking agent) present in the dusting mix may include any of those employed in the coating syrup and set out above. The preferred sweetener present in the dusting mix will be sorbitol.

In preferred embodiments, the weight ratio of the solids present in the coating syrup to the dusting mix will range from about 5:1 to about 20:1.

Generally, a single deposition of each of the coating syrup and the dusting mix may not be sufficient to provide the desired amount or thickness of coating deposited on the comestible. Accordingly, it usually will be necessary to apply second, third or more coats of each of the coating syrup and dusting mix in order to build up the weight and thickness of the coating to desired levels. However, before applying subsequent layers of first coating syrup, the previously applied layers of coating syrup are allowed to dry, for example, by gently flowing air at a temperature of from about 68° to about 88° F. and having a relative humidity of from about 20 to about 40% and flowing at a volume (36" pan) of from about 400 to about 500 cfm. For example, in coating chewing gum, the applications of coating syrup and dusting mix are continued until the average gum piece weight reaches about 90% of the required coated weight. Thus, if the coating is to comprise about 35% by weight of the coated chewing gum tablet, application of 10 to 12 coats of coating syrup and 7 to 9 coats of dusting mix may be required. The last three coats should preferably be coating syrup by itself, without dusting mix.

It will be appreciated that the number of applications required will also vary depending upon the amount of solids present in the coating syrup, the amount of dusting mix employed, and the type of comestible to be coated.

After a sufficient amount of coating has been applied to the pieces of comestible to be coated, the coating on the pieces will be smooth and polished and otherwise finished without the need for applying a second coating syrup or finishing syrup.

Flavoring in the form of liquid flavor may be added with the coating syrup, while spray dried flavors may be added with the dusting mix. The flavoring will preferably be applied after an initial coating syrup-dusting mix has been applied.

In the case where the comestible to be coated is chewing gum, flavoring may be added to the gum base. The flavoring in the gum center will be present in an amount within the range of from about 0.5 to about 1.5%, and preferably from about 0.7 to about 1.2% by weight of the gum center. The flavoring in the coating will be present in an amount within the range of from about 0.5 to about 5% and preferably from about 1.25 to about 4% by weight of the coating. Such flavoring may comprise oils derived from plants, leaves, flowers, fruit, etc. Representative flavor oils of this type include citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, as well as the following essential oils: peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen). Various synthetic flavors, such as mixed fruit, may also be incorporated in the chewing gum of the invention with or without conventional preservatives.

Sweeteners suitable for use herein which may be present in the gum center and/or coating may comprise natural or synthetic sugar substitutes.

Where employed, the synthetic sweeteners may be present in the chewing gum center in an amount within the range of from about 0.04 to about 2% and preferably from about 0.4 to about 0.8% by weight of the chewing gum. Examples of synthetic sweeteners suitable for use herein include free saccharin acid, sodium, calcium or ammonium saccharin, cyclamate salts, dihydrochalcones, glycyrrhizic acid and salts, L-aspartyl-L-phenylalanine methyl ester, the sodium or potassium salt of 3,4-dihydro-6-methyl-1,2,3-oxathiazine-4-one-2,2-dioxide (Acesulfone-K), and mixtures thereof.

Where employed, natural sugars and/or natural sugar substitutes may be present in the chewing gum center in an amount within the range of from about 0.05 to about 90%, and preferably from about 10 to about 85% by weight of the chewing gum. Such natural sweeteners suitable for use herein include sugar alcohols, such as, sorbitol, xylitol, mannitol, isomaltitol, or maltitol. If desired, sugars such as sucrose, or dextrose may also be employed.

The gum base will be present in an amount within the range of from about 10 to about 60%, and preferably from about 15 to about 45% by weight.

In general, the gum base is prepared by heating and blending various ingredients, such as natural gums, synthetic resins, waxes, plasticizers, etc., in a manner well known in the art. Typical examples of the ingredients found in a chewing gum base are masticatory substances of synthetic origin such as styrene-butadiene copolymer, isobutylene-isoprene copolymer, polyisobutylene, polyethylene, petroleum wax, polyvinyl acetate, as well as masticatory substances of natural origin such as rubber latex solids, chicle, crown gum, nispero, rosidinha, jelutong, pendare, perillo, niger gutta, tunu, etc. The elastomer or masticatory substance will be employed in an amount within the range of about 5 to about 15%, preferably from about 8 to about 12%, and optimally from about 9 to about 11% by weight of the gum base composition.

The gum base may also include solvents, detackifiers, waxes, softening agents, lubricants, fillers, emulsifiers, colorants, antioxidants and/or texturizers, bulking agents and other conventional ingredients as will be apparent to those skilled in the art. Examples of typical gum bases suitable for use herein are disclosed in U.S. Pat. Nos. 3,052,552 and 2,197,719.

As indicated, in addition to chewing gum, the comestible to be coated may include any edible solid, such as candies, including hard candies and pressed candies, jelly beans, peanuts, other confections, as well as pills, tablets or other solid dosage forms for medicinal or therapeutic use.

A preferred coating, in accordance with the present invention, for a sugarless chewing gum will have the following composition.

| Ingredient | Parts by weight of coating |
| --- | --- |
| Sorbitol | 45 to 90 |
| Mannitol | 2 to 25 |
| Gum arabic | 0.25 to 3 |
| Calcium carbonate | 2 to 20 |
| Titanium dioxide | 0.1 to 5 |

The following Examples represent preferred embodiments of the present invention.

EXAMPLES 1 TO 3

Sugarless-coated sugarless chewing gums having center or core portions as shown in Table I and coatings as shown in Table II below are prepared as follows.

TABLE I

Composition of Gum Center or Core
(present in all chewing gum Examples)

| Ingredient | Parts by Weight |
| --- | --- |
| Gum base | 24 |
| Sorbitol-powder | 49 |
| Sorbitol liquid (68–70% sorbitol) | 25 |
| Yelkin | 0.5 |
| Flavor | 2 |

TABLE II

Composition of Various Coating Mixtures
Required for Forming Coating
on Gum Centers of Table I Parts by Weight

| | Example No. | | |
| --- | --- | --- | --- |
| | 1 | 2 | 3 |
| Coating Syrup | | | |
| Gum arabic solution (48%) | 18 | 20 | 24 |
| Gelatin solution (20%) | 0 | 30 | 15 |
| Sorbitol liquid (68–70%) | 55 | 50 | 60 |
| Hydrogenated starch hydrolysate | — | 30 | 10 |
| Mannitol | 7 | 6 | 5 |
| Calcium carbonate powder | 7 | 8 | 5 |
| Titanium dioxide powder | 5 | 4 | 6 |
| Hot water (160° F.) | 9 | 11 | 13 |
| Color (as needed) | | | |
| Dusting Mix | | | |
| Sorbitol (crystalline powder) | 70 | 70 | 70 |
| Mannitol powder | 15 | 15 | 15 |
| Calcium carbonate powder | 7.5 | 10 | 5 |
| Titanium dioxide powder | 7.5 | 5 | 10 |

The chewing gum centers are prepared as follows:

Gum base is melted and maintained at a temperature within the range of 150°–175° F. Softener is added and then the solid sugar alcohols are added slowly with stirring. Thereafter, liquid flavor is added and the mixture is stirred until homogeneous. Sugar alcohols are slowly added and then artificial and/or natural sweetener (where employed).

Where spray dried flowers are employed, they are added with the artificial sweeteners.

The above mixture is stirred until homogeneous, cooled, rolled and scored and individual pieces or pillows are produced.

The coating mixture is prepared by mixing the various ingredients, under heating if necessary, to form a well-mixed suspension.

The dusting mix is prepared by simply mixing the various ingredients and until a substantially homogeneous mixture is formed.

The gum centers to be coated are placed in a standard revolving coating pan. The gum pieces are dedusted using cool dry air. The coating syrup mixed and warmed to a temperature of 120° F. is applied to the gum pieces. After about 2-3 minutes, the dusting mix is applied to the gum pieces coated with the coating syrup. The gum pieces are allowed to cool for 2 minutes to absorb the dusting mix. The gum pieces are then dried by contact with gently flowing air at a temperature of about 78° F., and having a relative humidity of about 30% and at a volume of air (36" pan) of about 450 cfm, for 2 minutes.

The above coating steps are repeated until the weight of an average gum piece reaches about 90% of the required coated weight. For example, if the required coated weight is 35%, 7 to 10 applications of the dusting mix are needed (the last 3 applications are of other coating syrup without the dusting mix) to reach an average piece weight of 1.5 g.

The so-coated gum pieces may then be polished and otherwise finished employing conventional means to produce sorbitol coated sugarless chewing gum having a soft chew with good sweetness and flavor release properties.

EXAMPLES 4 AND 5

Sugarless coated sugarless candy, having a center or core portion as shown in Table III below and a coating as shown in Table II of Example 1, is prepared employing the following procedure.

TABLE III

| Composition of Candy Center | |
|---|---|
| Ingredient | Amount (Parts by Weight) |
| Hydrogenated starch hydrolysate syrup (78% solids, including 6% sorbitol and 50% mannitol) | 97 |
| Sorbitol syrup | 2 |
| Malic acid | 1 |
| Cherry Flavor | 0.25 |
| Color | 0.4 |

The hydrogenated starch hydrolysate and sorbitol syrups are fed into the top of a mixing kettle and are cooled under constant slow agitation to 330°-335° F. The coloring agent is added at 280°-300° F. The mix is dropped at 25" Hg and held under vacuum for 10 minutes. The hot mix is then transferred to a mixing table where malic acid and flavor are added with mixing. The candy mix is allowed to cool to 160°-170° F. and is tabletted.

The coating is applied as described in Examples 1 to 3 to produce a pleasant tasting sugarless coated sugarless candy.

In a manner similar to that described in Examples 1 to 5 any type pill or tablet or other solid shape may be coated with a sugarless coating in accordance with the present invention.

What is claimed is:

1. A method for preparing a sugarless coated chewing gum or candy, which comprises the steps of applying to center portions of said chewing gum or candy a coating syrup comprising an aqueous solution of from about 30 to about 70% by weight of a normally sweet non-sugar hygroscopic material selected from the group consisting of sorbitol, mannitol, maltitol, isomaltitol, hydrogenated starch hydrolysate and mixtures thereof, from about 5 to about 30% by weight of a binder, from about 3 to about 15% by weight of an anti-sticking compound, and from about 2 to about 12% by weight of a dispersing agent and applying to said so-treated center portions a coating dusting mix comprising said normally sweet non-sugar hygroscopic material in dry form, at least a portion of said dry hygroscopic material being absorbed on the coating syrup applied to said center portions to form a coating on said center portions.

2. The method as defined in claim 1 wherein said steps of applying said coating syrup and then applying said coating dusting mix are repeated, as necessary, to build up a coating of desired thickness on the center portions.

3. The method as defined in claim 2 further including the step of applying said coating syrup as the last 2 to 4 coats to said center portions previously coated with said coating syrup and said coating dusting mix, said lastly applied coating syrup comprising said normally sweet hygroscopic material and serving to smooth out and providing a shine to the coating of said normally sweet hygroscopic material previously applied to said center portions.

4. The method as defined in claim 1 wherein said coating dusting mix contains a moisture absorbing agent, an anti-sticking agent, and a dispersing agent.

5. The method as defined in claim 1 wherein said coating syrup comprises liquid sorbitol, gum arabic solution, calcium carbonate, titanium dioxide and mannitol, and said coating dusting mix comprises sorbitol powder, mannitol powder, calcium carbonate and titanium dioxide.

6. A method as defined in claim 1 wherein said center portion comprises chewing gum or candy.

7. The method as defined in claim 1 wherein said center portion is sugarless chewing gum.

8. The method as defined in claim 1 wherein said coating syrup further includes a film-forming agent which comprises gelatin, methyl cellulose, hydroxypropyl cellulose, ethyl cellulose, hydroxyethyl cellulose, and/or carboxymethyl cellulose.

9. The method as defined in claim 1 wherein said binder for imparting cohesivity to the coating ingredients is gum arabic, xanthan gum, gum tragacanth, tapioca dextrin, or modified food starch.

10. The method as defined in claim 1 wherein said anti-sticking agent is calcium carbonate, talc, or magnesium trisilicate.

11. The method as defined in claim 1 wherein said dispersing agent is titanium dioxide.

12. The method as defined in claim 1 wherein said center portion is candy.

13. The method as defined in claim 1 wherein said center portion is chewing gum and said coating applied is comprised of sorbitol as said hygroscopic material, gum arabic as a binder, calcium carbonate as an anti-sticking-diluent compound, titanium dioxide as a dispersing agent and mannitol as a moisture absorbing agent.

* * * * *